(12) United States Patent
Lee

(10) Patent No.: US 7,037,284 B2
(45) Date of Patent: May 2, 2006

(54) SPECIFIC PELVIC COMPRESSION BELT

(76) Inventor: Diane Lee, 3515 Canterbury Drive, Surrey, British Columbia, V35 0G8 (CA)

( * ) Notice: Subject to any disclaimer, the term of this patent is extended or adjusted under 35 U.S.C. 154(b) by 388 days.

(21) Appl. No.: 10/328,681

(22) Filed: Dec. 23, 2002

(65) Prior Publication Data

US 2003/0149390 A1 Aug. 7, 2003

Related U.S. Application Data

(60) Provisional application No. 60/350,149, filed on Jan. 17, 2002.

(51) Int. Cl.
*A61F 5/00* (2006.01)
(52) U.S. Cl. .................................................. 602/19
(58) Field of Classification Search .................. 602/19, 602/5, 1, 61, 60, 41; 128/876; 2/311, 464, 2/465
See application file for complete search history.

(56) References Cited

U.S. PATENT DOCUMENTS

| | | | | |
|---|---|---|---|---|
| 4,576,154 A | | 3/1986 | Hyman et al. ................ 128/78 |
| 4,677,699 A | * | 7/1987 | Barabe ........................... 2/221 |
| 4,747,399 A | * | 5/1988 | Glomstead ................... 602/36 |
| 4,836,194 A | * | 6/1989 | Sebastian et al. ............. 602/19 |
| 5,016,291 A | * | 5/1991 | Capper ........................... 2/312 |
| 5,086,759 A | | 2/1992 | Buddingh ..................... 602/19 |
| 5,176,131 A | * | 1/1993 | Votel et al. .................... 602/19 |
| 5,205,815 A | * | 4/1993 | Saunders ....................... 602/19 |
| 5,388,274 A | | 2/1995 | Glover et al. ................... 2/338 |
| 5,399,151 A | * | 3/1995 | Smith ............................ 602/19 |
| 5,421,809 A | * | 6/1995 | Rise ............................... 602/19 |
| 5,464,136 A | * | 11/1995 | Eddy .......................... 224/666 |
| 5,484,395 A | | 1/1996 | DeRoche ..................... 602/19 |
| 5,489,260 A | * | 2/1996 | Striano ......................... 602/19 |
| 5,536,246 A | * | 7/1996 | Saunders ..................... 602/19 |
| 5,551,085 A | | 9/1996 | Leighton ......................... 2/44 |
| 5,586,969 A | * | 12/1996 | Yewer, Jr. .................... 602/19 |
| 5,591,122 A | * | 1/1997 | Yewer, Jr. .................... 602/19 |
| 5,628,725 A | * | 5/1997 | Ostergard ..................... 602/62 |
| 5,683,022 A | * | 11/1997 | Evans ......................... 224/583 |
| 5,728,056 A | * | 3/1998 | Seriguchi et al. ............. 602/19 |
| 5,776,087 A | | 7/1998 | Nelson et al. ................ 602/19 |
| 5,785,672 A | * | 7/1998 | Mattison et al. .............. 602/19 |
| 5,833,638 A | * | 11/1998 | Nelson ......................... 602/19 |
| 5,867,836 A | * | 2/1999 | Quinones ....................... 2/236 |
| 5,943,705 A | * | 8/1999 | Sink ............................... 2/338 |
| 5,970,526 A | * | 10/1999 | Weathers ........................ 2/321 |

(Continued)

OTHER PUBLICATIONS

U.S. Appl. No. 60/350,149, filed Jan. 17, 2002, Lee.

*Primary Examiner*—Danton D. DeMille
*Assistant Examiner*—Huong Q. Pham
(74) *Attorney, Agent, or Firm*—Vidas, Arrett & Steinkraus, PA

(57) ABSTRACT

A pelvic compression belt may be comprised of a belt body constructed and arranged for positioning relative to a pelvic region of a human body. The pelvic belt may have at least one tightening member constructed and arranged to be independently and removably engaged to said belt body. Each tightening member may have identical or varying levels of elasticity. Furthermore, each tightening member may be positioned at any desired location about said belt body to provide anterior and/or posterior compressive forces for treatment of muscular and/or joint dysfunction.

18 Claims, 5 Drawing Sheets

U.S. PATENT DOCUMENTS

| | | | |
|---|---|---|---|
| 6,066,108 A | 5/2000 | Lundberg | 602/23 |
| 6,213,968 B1 | 4/2001 | Heinz et al. | 602/19 |
| 6,440,094 B1 * | 8/2002 | Maas | 602/5 |
| 6,610,032 B1 * | 8/2003 | Prody | 604/179 |
| 6,755,799 B1 * | 6/2004 | Toda | 602/19 |
| 6,766,532 B1 * | 7/2004 | Cabana | 2/44 |

* cited by examiner

SPECIFIC PELVIC COMPRESSION BELT

CROSS-REFERENCE TO RELATED APPLICATIONS

This application claims priority from the provisional application No. 60/350,149 filed Jan. 17, 2002 which is incorporated by reference herein in its entirety.

STATEMENT REGARDING FEDERALLY SPONSORED RESEARCH

Not Applicable

FIELD OF THE INVENTION

The present invention relates to an orthopedic pelvic compression belt for stabilization of specific aspects of the pelvic girdle.

BACKGROUND OF THE INVENTION

The transversus abdominis muscle has a unique function that works independently from the other abdominal muscles. This muscle contributes to
  a) the control of the lumbar spine and pelvic girdle and
  b) the ability to generate stiffness in a non-specific direction of the lumbar spine and pelvic girdle.

Normally, the transversus abdominis muscle contracts before the other abdominal muscles and before movement occurs. This muscle contracts along with the multifidus muscle in order to prepare the spine and pelvic girdle for the impending movement and to prevent excessive translation or shear from occurring between the joints of the low back and pelvic girdle.

Intersegmental lumbar stability and stability of the pelvic girdle is enhanced by increasing the stiffness of the intersegmental and sacroiliac joints/pubic symphysis. The multifidus and transversus abdominis muscles attach directly to the spine and have been shown to create more than two-thirds of the increase in stiffness at the L4-5 (lumbar) segment for most individuals. The multifidus muscle attaches directly to the sacrum and the transversus abdominis muscle indirectly crosses the pelvic girdle (sacroiliac joints) through the thoracodorsal fascia. The co-activation of transversus abdominis and multifidus muscle have recently been shown to increase the stiffness of the sacroiliac joints of the pelvic girdle through these anatomical attachments. In this manner, shear forces through the spine and sacroiliac joints may be controlled and load transferred through the trunk and pelvic girdle to the lower extremities. Instability of the spine and/or pelvic girdle occurs when local muscles such as the multifidus and transversus abdominis are dysfunctional.

Stabilization of the pelvic girdle and lumbar spinal region requires compression of the sacroiliac joints and pubic symphysis by the activation of the deep abdominal muscles (transversus abdominis), the deep back muscles (multifidus) and the pelvic floor muscles. Many patients having lower back or pelvic pain often have a dysfunction of these muscles. These dysfunctions are typically of several varieties. One such dysfunction is a significant delay in the contraction of the transversus abdominis and/or multifidus muscles. When this contraction is delayed there is a failure to prepare the spine/pelvic girdle for the movement of the prime mover. Loss of independent control or consistent control of natural or high speed movements are also dysfunctions of these muscles. Treatment requires specific exercise instruction for retraining of proper muscle function. This includes restoring the appropriate recruitment patterning or timing of muscle contraction, muscle strength and endurance. Upon retraining of these muscles, lower back or pelvic pain is often alleviated.

During the muscular retraining process the patient may yet be in pain due to the dysfunction of these muscles, and the relative instability of the pelvic girdle. It has been found that one of the major causes of this type of back and sacroiliac pain is lack of motion control due to insufficient stiffness of the sacroiliac joints. In this condition, too little compression is generated within the pelvic girdle by the local muscles to control the vertical and anteroposterior shear forces which occur during activities of daily living such as walking, sitting and/or bending. This excessive translation leads to irritation of the local soft tissues and perpetuates the pain. The presence of pain has been shown to inhibit these local stabilizing muscles (transverses abdominis and multifidus). Thus, an outside compressive force as exerted by the instant invention is needed to increase the intrapelvic stiffness, assist in the control of shear forces and thus reduce the local pain. The instant invention therefore facilitates the training of the local stabilizers ultimately expediating recovery.

Many orthopedic belts have been used to attempt to protect against back injury and pain. However, these belts are generally worn in a position which is too high relative to an individual's back to be effective for relieving pelvic pain. The majority of these are back braces used for support of the lumbar region of the spine.

Frequently, it is necessary for compression to be applied to the pelvic girdle. The inventive belt described herein is typically positioned around the pelvic girdle of an individual between the greater trochanters of the femurs and the iliac crest of the innominate bones. The instant invention provides the necessary compressive force to the sacroiliac joint/pubic symphysis and provides an adjustable amount of force in a variety of specific locations, thereby allowing a practitioner to customize the belt for the specific needs of the patient. The belt provides minimal fitting requirements as it is adjustable and may accommodate the varied pelvic sizes of individuals.

Without limiting the scope of the invention a brief description of some of the claimed embodiments of the invention are set forth below. Additional details of the disclosed embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF DESCRIPTION OF THE INVENTION

The present invention relates to an orthopedic belt. Embodiments of the Specific Pelvic Compression Belt apply compression to specific aspects of the pelvic girdle. In patients with muscle dysfunction in the deep abdominals, the deep back muscles, and the pelvic floor muscles, the Specific Pelvic Compression Belt may be utilized in the strengthening rehabilitation of these muscles. The location of the compression varies according to the individual's pattern of muscle dysfunction rendering the belt very useful for treatment of an individual patient's needs.

An advantage of the present invention is the provision of a belt body which is adapted for positioning at any location relative to the pelvic region of an individual.

Another advantage of the present invention is the provision of one or more independently adjustable tightening members which may be released and/or removably engaged to a pelvic belt body.

Still another advantage of the present invention is the provision of a specific pelvic compression belt which may be formed of elastic and/or inelastic materials.

Still another advantage of the present invention is the provision of a specific pelvic compression belt having a fastener which may be a buckle, a snap, a cord, hook and loop material, and adhesive, and/or any combination thereof.

Still another advantage of the present invention is the provision of a specific pelvic compression belt where the fastener is adapted to be circumferentially engaged to the belt.

Still another advantage of the present invention is the provision of a specific pelvic compression belt where the tightening members include fasteners.

Still another advantage of the present invention is the provision of a specific pelvic compression belt where the tightening members are adapted for independent tightening relative to the belt body.

Still another advantage of the present invention is the provision of a specific pelvic compression belt where the tightening members have straps and each of the straps includes a fastener constructed for affixation to the belt body.

Still another advantage of the present invention is the provision of a specific pelvic compression belt where the straps are formed of elastic materials and each of the straps may include elastic material having different elasticity properties.

Still another advantage of the present invention is the provision of a specific pelvic compression belt where each of the tightening members may be different lengths to facilitate compression of the sacroiliac joint and muscle therapy for an individual.

Still another advantage of the present invention is the provision of a specific pelvic compression belt having more than two tightening members which are used to facilitate compression of the sacroiliac joint and muscle therapy for an individual.

Still another advantage of the present invention is the provision of a specific pelvic compression belt where the tightening members are positioned relative to the belt body to provide or prevent overlap of the belt members relative to the belt body and the respective tightening members.

Still another advantage of the present invention is the provision of a specific pelvic compression belt where the tightening members may be continuously engaged to the exterior of the belt body for compression of the sacroiliac joint, which in turn promotes muscle therapy for an individual.

Still another advantage of the present invention is the provision of a specific pelvic compression belt where the tightening members may alternatively overlap one another during compression of the sacroiliac joint and during muscle therapy for an individual.

DETAILED DESCRIPTION OF THE PREFERRED EMBODIMENTS

Figure 1:
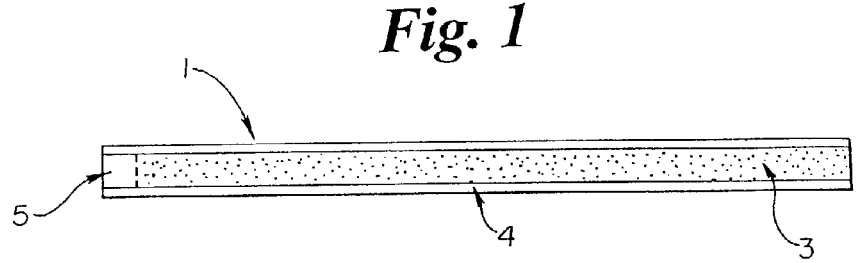
FIG. 1 illustrates a back view of the belt body.
Figure 3:
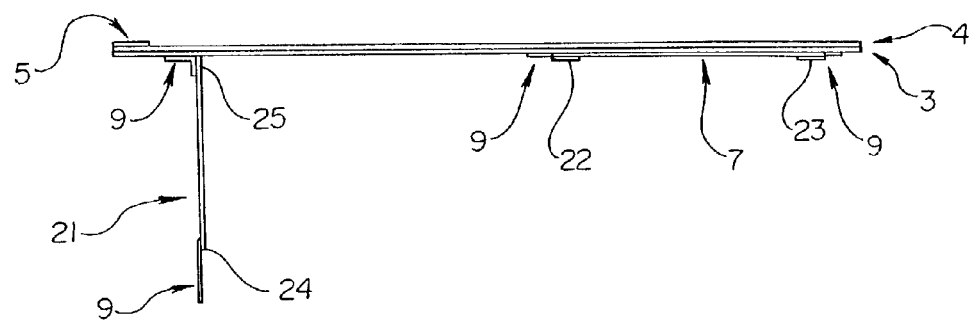
FIG. 3 illustrates a top elevational view of the belt body with one side panel strap fully attached and with one side panel strap having only one end attached.
Figure 7:
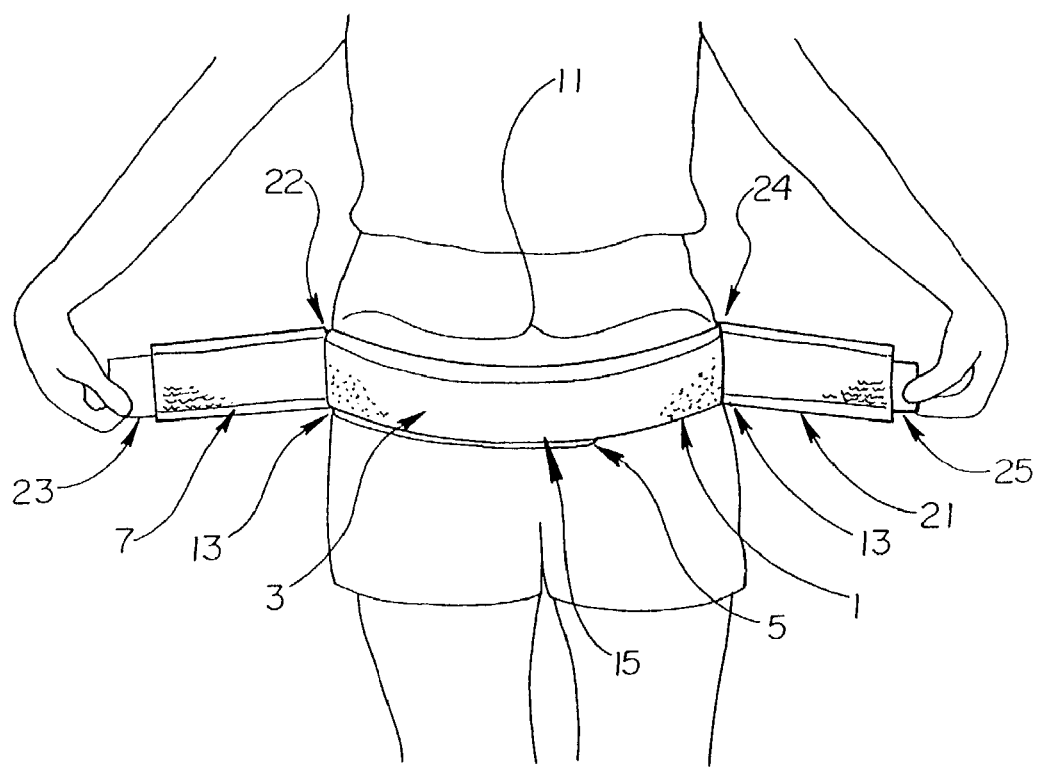
FIG. 7 illustrates the belt while being worn prior to engagement of the elastic side panel straps.

The specific pelvic compression belt hereinafter identified as SPC belt includes belt body 1 as shown in FIG. 1. Belt body 1 may be formed of inelastic material base 4 solely or in combination with attachment surface 3 attached to material base 4. The belt body 1 may be positioned and engaged about the pelvic girdle between the greater trochanters of the femurs and the iliac crest of the innominate bones of an individual. Belt body 1 may be closed about the pelvic girdle with front attachment fastener 5 (FIGS. 1, 3, 7). Buckles, zippers, snaps, buttons, hooks, magnets, adhesives, and cords or any combination thereof are contemplated as possible front attachment fasteners 5, yet hook and loop material such as Velcro® is preferred.

The material base 4 of the belt body 1 may be formed of an inelastic loop material to which the hook fasteners attach directly. The side panel straps 7, 21 respectively can be attached directly to belt body 1.

Alternatively, attachment surface 3 may be a longitudinal strip of receiving hook or loop fabric material attached along the length of the material base 4 of the belt body 1, for coupling to one or more side panel straps 7, 21 respectively.

Figure 2:
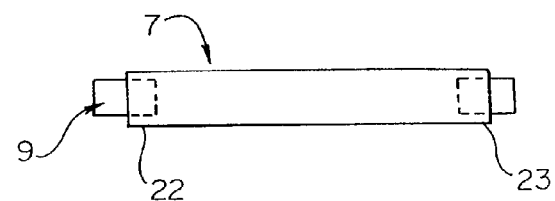
FIG. 2 illustrates a front view of an elastic strap.

As shown in FIG. 2 the first side panel strap 7 is made of an elastic material and includes fasteners 9 (preferably hook and loop) on each of the first end 22 and second end 23. This allows either the first or second ends 22, 23 respectively of the side panel straps 7 to be positioned at any location along the circumference of body 1. Initially attachment of either the first end 22 or the second end 23 to the body 1 may occur by coupling of the mating hook and loop fasteners 9 to the attachment surface 3 of belt body 1. The unengaged end of the first side panel strap 7 may then be attached at another location on belt body 1 according to an individual's pattern of muscular dysfunction by placing a desired amount of stretching/tension to the elastic material of the first side panel strap 7 and then affixing the fasteners 9 of the second end 23 to another location along the belt body 1.

FIG. 3 shows a top elevational view of the combination of a belt body 1 with the first side panel strap 7 fully attached at both the first and second ends 22, 23 respectively and with a second side panel strap 21 having only a first end 25 attached. The belt described herein provides for a sleek and non-bulky device which may be worn under clothing. The first and second end attachments 22, 23, the front attachment fastener 5, and the receiving hook and loop material of belt body 1 may be formed of a thinner material than is illustrated in relation to the belt body in FIG. 3.

Figure 4:
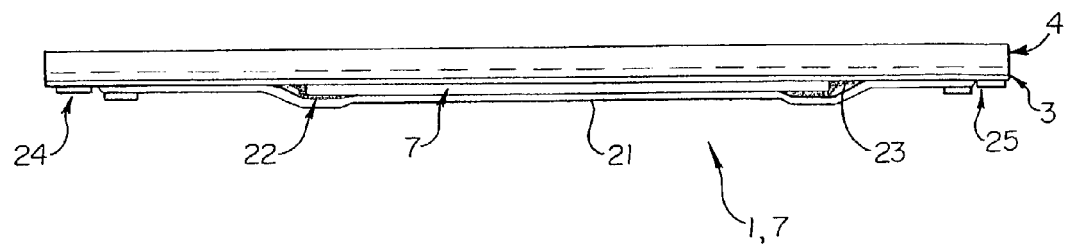
FIG. 4 illustrates a top elevational view of a portion of the belt body with a first side panel strap fully attached and a second longer strap fully attached atop the first side panel strap.

FIG. 4 illustrates a top elevation view of a portion of belt body 1 with a first side panel strap 7 fully attached and a second longer side panel strap 21 fully attached on top of the first side panel strap 7. In this example, the compression force of the first side panel strap 7 and the different compression force of the second side panel strap 21 are combined such that the elastic forces of strap 7 and strap 21 may be localized to the same approximate area under the shorter first side panel strap 7. First side panel strap 7 is attached by coupling the first end 22 and second end 23 to the belt body 1. The second longer side panel strap 21 may be placed over and extends beyond the shorter first side panel strap 7. The longer second side panel strap 21 may be held in place by coupling of the first end 24 and the second end 25 to the belt body 1 beyond the respective first end 22, and respective second end 23 of the first side panel strap 7. Because the first side panel strap 7 and the second side panel strap 21 are thin, the respective side panel straps continue to be non-bulky when attached to the body 1. The second side panel strap 21 may be independently removable with respect to the first side panel strap 7 permitting positioning and engagement of the second side panel strap 21 on the belt body 1 entirely or partially over the first side pane strap 7 as it continues to overlay the first side panel strap 7, to eliminate bulkiness, while at the same time allowing the practitioner to easily customize the respective individual compression of the first side panel strap 7 and the second side panel strap 21 for treatment of any muscle and/or joint condition. Examples of patients who might benefit from this feature are those with excessive weakness of a particular muscle in relation to the others around the pelvic girdle.

Figure 5:
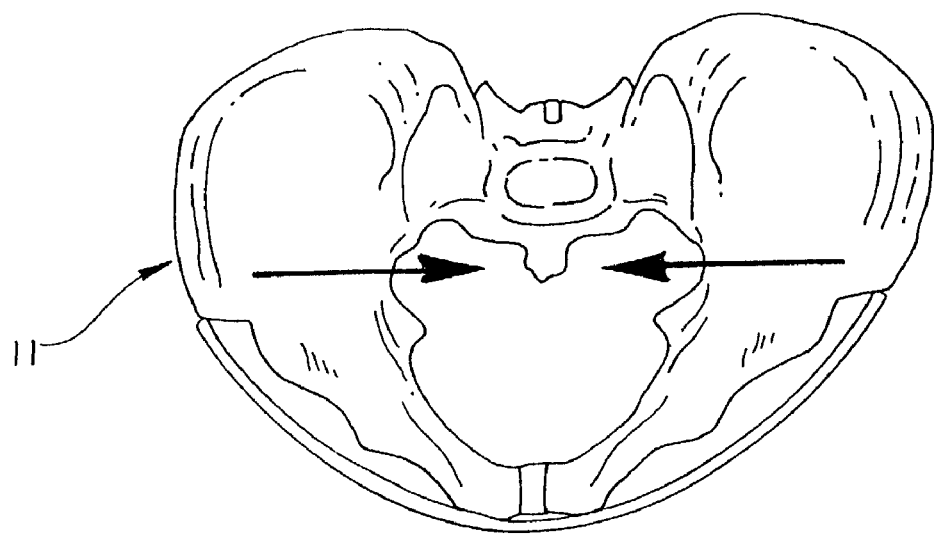
FIG. 5 illustrates compression on the pelvic girdle provided by contraction of the transverses abdominis.

The elastic first and second side panel straps 7, 21 respectively may provide compression in specific desired locations about the pelvic girdle 11 following engagement of the body 1 about an individual. FIG. 5 illustrates compression of the pelvic girdle 11 when the deep abdominal muscles (transversus abdominis) are properly activating and providing a compressive force to the pelvic girdle 11.

FIG. 7 illustrates the belt body 1 as engaged about the pelvic girdle 11 prior to the engagement of both fasteners of either the elastic first or second side panel straps 7, 21 respectively and prior to the placement of tension on either the first or second side panel straps 7, 21 for exertion of compression about the pelvic girdle 11. In FIG. 7, fastener 22 of strap 7 is attached to side location 13 preferably using hook and loop material. Fastener 24 of strap 21 is similarly attached onto the other side of the pelvis. Upon engaging fastener 22 of strap 7 and/or fastener 24 of strap 21, the unengaged fasteners 23 and/or 25 (preferably of the hook and loop variety) of each elastic first and second side panel straps 7, 21 may be attached anywhere along the belt body 1 up to the anterior midline 15. This is done by stretching each strap 7, 21 to a specific tension and affixing it posteriorly proximate to the anterior midline 15 in the case when the deep abdominal muscles are in dysfunction bilaterally. This procedure provides anterior compression force to the pelvic girdle 11. Additional straps can also be used to incrementally adjust or increase the compressive force. Straps having different compressive forces or lengths may also be used.

Figure 8:
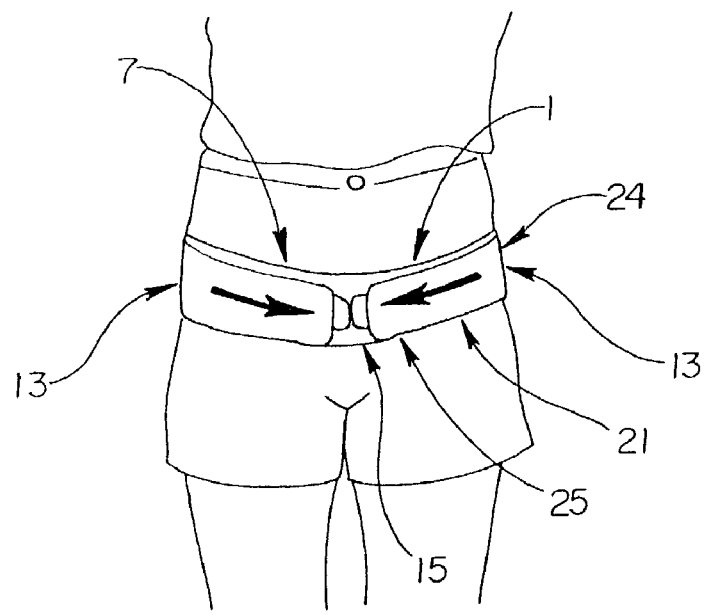
FIG. 8 illustrates the belt with the side panel straps positioned anteriorly to provide compression anteriorly (simulating a contraction of the transversus abdmonis).

FIG. 8 illustrates initiation of a compressive force when the transversus abdominis are bilaterally dysfunctional. In this embodiment, a compressive force may be established by attaching first end 22 of the elastic first side panel strap 7 to the body 1 proximate to a side location 13 along the human pelvis and then stretching the elastic first side panel strap 7 anteriorly and attaching second end 23 proximate to the anterior midline 15 of the pelvis at the horizontal level of the anterior superior iliac spines. Repeating of the steps may occur with an elastic second side panel strap 21 attached to body 1 proximate to opposite side location 13 along the human pelvis and then stretching the elastic side panel strap 21 anteriorly and attaching secured end 25 proximate to the anterior midline 15 of the pelvis at the horizontal level of the anterior superior iliac spines. The elastic first and second side panels 7, 21 may be stretched so as to provide independent and variable compression force between each of the first and second side panel straps 7, 21 respectively. Further, variable compressive force may be customized by use of a combination of short, long and/or short and long first and second elastic side panel straps 7, 21 where the first side panel strap 7 may be adapted for positioning under a longer second side panel strap 21 and/or the first and second side panel straps 7, 21 respectively may be adapted for positioning about body 1 without placement in an overlaying relationship.

Figure 6:
FIG. 6 illustrates compression on the pelvic girdle provided by contraction of multifidus.

FIG. 6 illustrates compression on the pelvic girdle 11 when the deep back muscles (multifidus) are properly activating and providing a compressive force to the pelvic girdle 11. When the deep back muscles (multifidus) are in dysfunction bilaterally, the SPC belt may be configured in an alternative embodiment to provide a posterior compression force to the pelvic girdle 11. Posterior compression may be achieved by using the first and second elastic side panel straps 7, 21 respectively.

Figure 9:
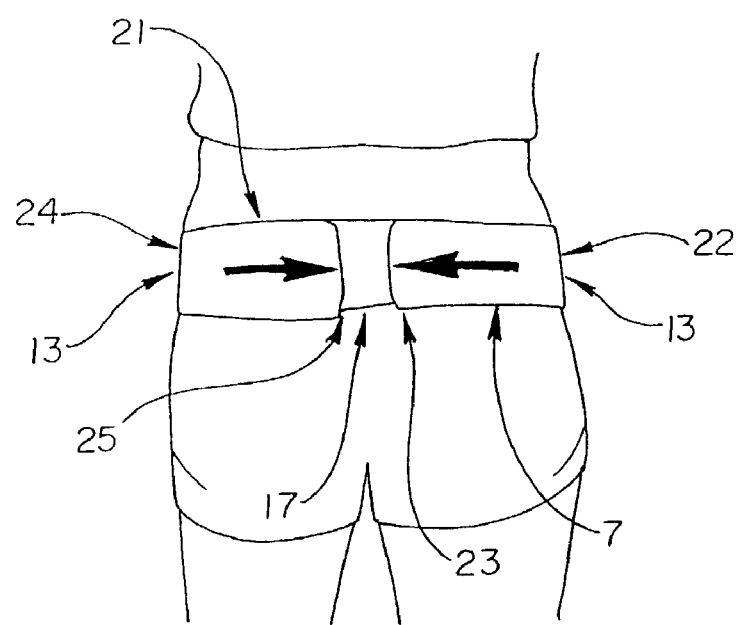
FIG. 9 illustrates the belt with the side panel straps positioned posteriorly to provide compression posteriorly (simulating a contraction of the multifidus).

FIG. 9 illustrates one embodiment for activating a compressive force when multifidus is bilaterally dysfunctional. As shown in FIG. 9, a posterior compression force may be achieved by attaching first end 22 of the first elastic side panel strap 7 to the body 1 in a side location 13 along the human pelvis and then stretching the first elastic side panel 7 posteriorly and attaching the second end 23 at the posterior midline 17 of the pelvis at the horizontal level of the posterior superior iliac spines. These steps may be repeated on the opposite side by attachment of the first end 24 of the second side panel strap 21 on the other side location 13 of the body 1. The second side panel strap 21 may also be stretched to provide a variable amount of compressive force for affixation of the second end 25 anteriorly proximate to the posterior midline 17. Further, variable compressive force may be customized by use of a combination of short, long and/or short and long first and second elastic side panel straps 21 where the first and second side panels straps 7, 21 are adapted for positioning on opposite sides of the body 1 and/or the positioning of the second elastic side panel strap 21 in complete or partial covering relationship on the first side panel strap 7 to facilitate multiplication of and/or the provision of a desired level of compression force to one side of the body 1 as compared to the opposite side of the body 1. It should be noted that one, two, three or more side panel straps 7, 21 may be coupled on each side of belt body 1 to provide a desired level of compressive force along any location about the pelvic girdle 11. It should be further noted that the first and second side panel straps 7, 21 are not required to be positioned on opposite sides of body 1 and may be positioned adjacent to each other to facilitate treatment of an individual.

Figure 10:
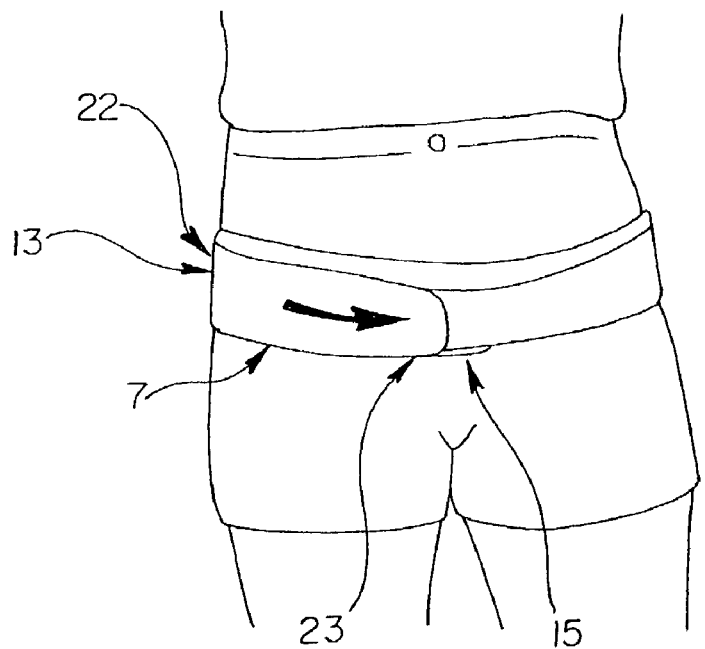
FIG. 10 illustrates the belt with one side panel straps positioned anteriorly.
Figure 11:
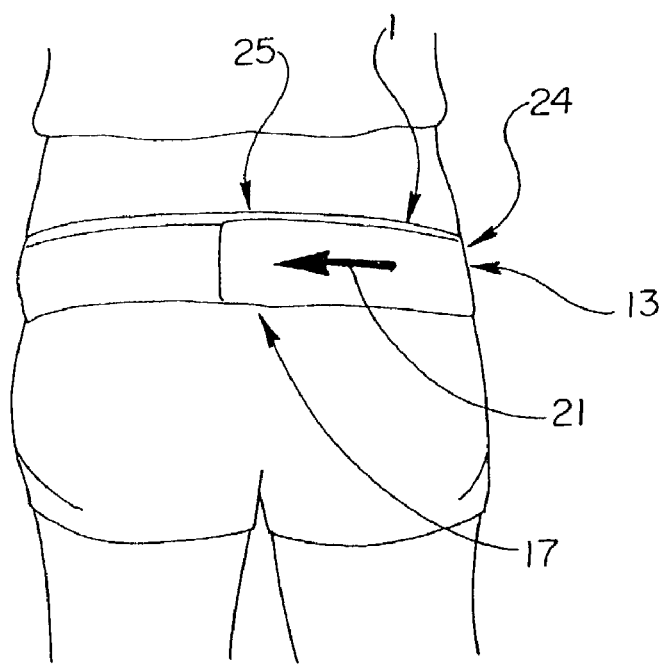
FIG. 11 illustrates the belt with one side panel straps positioned posteriorly.

When one transversus abdominis and one multifidus are in dysfunction unilaterally, the SPC belt may be configured in an alternative embodiment to provide both unilaterally anterior and unilaterally posterior compression force to the pelvic girdle 11 as shown in FIG. 10 and FIG. 11. Simultaneous unilateral anterior and unilateral posterior compression force may be accomplished through the use of the first and second side panel straps 7, 21 respectively. FIG. 10 and FIG. 11 illustrate one alternative embodiment for establishment of a compressive force when one transversus abdominis and one multifidus are dysfunctional. As shown in FIG. 10, first end 22 of first elastic side panel strap 7 may be attached to the body 1 proximate to a side location 13 along the human pelvis and then stretching of the first elastic side panel strap 7 anteriorly and attaching the second end 23 proximate to the anterior midline 15 of the pelvis at the horizontal level of the anterior superior iliac spines may occur. As shown in FIG. 11, attachment of the first end 24 of the second elastic side panel strap 21 proximate to the same side location 13 along the body 1 may occur. Stretching compression of the second side panel strap 21 may then occur posteriorly for coupling of second end 25 proximate to the posterior midline 17. The elastic material of the first side panel strap 7 and second side panel strap 21 may have varying elasticities and may be stretched to a greater or lesser degree so as to provide a variable amount of compressive force. It should be noted that the elastic material of the first side panel strap 7 may not be identical to the second side panel strap 21 thereby permitting different or multiple levels of compressive force about the body 1. Further, variable compression force may be customized by use of a combination of short, long and/or shorter and longer first and second elastic side panel straps 7, 21, where the first and second side panel straps 21 are adapted for positioning in any location about body 1. The positioning of the second elastic side panel strap 21 may be removed from or in complete or partial covering relationship over the first side panel strap 7 to facilitate the multiplication and/or other desired level of compressive force to be applied to one side of body 1 relative to the opposite side of body 1. It should be noted that one, two, three or more side panel straps 7, 21 may be coupled to body 1 to provide a desired level of compressive force at any location about the pelvic girdle 11 of an individual.

In an embodiment of this invention the belt body 1 is comprised of hook and loop material therefore the first and second ends 22 through 25 of the first and second side panel straps 7, 21 may thus be placed anywhere along the circumference of the belt.

Additional advantages of the disclosed invention are that the belt may be easily cleaned, is light weight, and is not bulky. The first and second side panel straps 7, 21 may be removed for cleaning and the entire device is made of lightweight material. The disclosed belt is for orthopedic use, therefore, most patients would prefer to not broadcast the fact that they are wearing such a device. This belt may be readily worn due to the sleek, non-bulky design. Because the first and second side panel straps 7, 21 are removable, they may be placed in such a way as to lie smoothly along the belt in either an anterior or posterior direction. Permanently attached straps are bulky in design because they have to work in two directions. Thus, there is an overlap and bend of material as the strap is forced into another direction or an inherent overlap and bend of material may exist. Having removable straps allows the material to be smoothly and continuously in contact the belt and to provide tension in an equal amount along the length of the belt as desired.

However, there may be instances in which multiple side panel straps may be used in which an overlap is desired. In making the precise adjustment to the compression about the pelvic girdle 11, it may be desirable to provide even more tension at a particular location and yet have some tension over a longer circumference. FIG. 4 illustrates a front elevational view of the belt body 1 with a first side panel strap 7 fully attached and a longer second side panel strap 21 fully attached atop the first side panel strap.

The above examples and disclosure are intended to be illustrative and not exhaustive. These examples and description will suggest many variations and alternatives to one of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The present invention may be embodied in other specific forms without departing from the spirit or essential attributes thereof, therefore, the illustrative embodiments should be considered in all respects as illustrative and not restrictive, reference being made to dependent claims rather than to the foregoing description to indicate the scope of the invention.

While this invention may be embodied in many different forms, there are described in detail herein specific preferred embodiments of the invention. This description is an exemplification of the principles of the invention and is not intended to limit the invention to the particular embodiments illustrated.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 2, or on claim 3; claim 6 may be taken as alternatively dependent from claim 5; etc.).

This completes the description of the preferred and alternate embodiments of the invention. Those skilled in the art may recognize other equivalents to the specific embodiment described herein which equivalents are intended to be encompassed by the claims attached hereto.

I claim:

1. A pelvic compression belt comprising:
   a) a belt body constructed and arranged for positioning relative to a pelvic region of a human body;
   b) a first tightening member comprising a first strap having a length and a pair of fasteners, the first tightening member comprising an elastic material having a first level of elasticity, the first tightening member constructed and arranged to be independently and removably engaged to said belt body and to be independently tightened with respect to said belt body; and c) a second tightening member comprising a second strap constructed and arranged to be independently and removably engaged to said belt body, the second tightening member overlapping the entire length of the first tightening member;

wherein said first strap and said second strap have different elasticity strengths.

2. The pelvic compression belt according to claim 1, wherein the belt is formed of an inelastic material.

3. The pelvic compression belt according to claim 1, wherein the belt is constructed and arranged for closure in one location relative to an individual.

4. The pelvic compression belt according to claim 1, said belt comprising a fastener selected from the group consisting of buckles, buttons, magnets, hooks, cords, snaps, zippers, drawstrings, hook and loop materials, and adhesives or any combination thereof.

5. The pelvic compression belt according to claim 4, wherein said fastener is constructed and arranged to be circumferentially engaged to the belt.

6. The pelvic compression belt according to claim 4, said second tightening member comprising a pair of fasteners.

7. The pelvic compression belt according to claim 1, said belt body comprising an attachment surface.

8. The pelvic compression belt according to claim 7, said attachment surface comprising hook or loop fabric material.

9. The pelvic compression belt according to claim 7, wherein said attachment surface spans an entire length of said belt body.

10. The pelvic compression belt according to claim 1, wherein said first tightening member and said second tightening member have different lengths.

11. The pelvic compression belt according to claim 1, wherein said first tightening member and said second tightening member have identical lengths.

12. The pelvic compression belt according to claim 1, comprising more than two tightening members.

13. The pelvic compression belt according to claim 1, wherein said first tightening member is constructed and arranged to continuously engage said belt body.

14. A method for correcting pelvic and sacroiliac joint dysfunction in an individual, comprising:

(a) positioning of a pelvic compression belt about the pelvic region of an individual, said pelvic compression belt comprising:

(i) a belt body;

(ii) a first tightening member comprising a first strap having a length and a pair of fasteners, the first tightening member comprising an elastic material having at least one level of elasticity, the first tightening member constructed and arranged to be independently and removably attached to said belt body and to be independently tightened with respect to said belt body; and (iii) a second tightening member comprising a second strap having a different elasticity than the first tightening member, the second tightening member constructed and arranged to be independently and removably attached to said belt body and to overlap the entire length of said first tightening member;

(b) adjusting the location of the pelvic compression belt relative to the pelvic girdle between the greater trochanters of the femurs and the iliac crest of the innominate bones; and (c) engaging the compressive effect by independently tightening the tightening members relative to the belt body and positioning said tightening members such that the second tightening member overlaps an entire length of the first tightening member.

15. A method according to claim 14 wherein said lightening members have different lengths.

16. The method according to claim 14 wherein said tightening members share compressive action for said pelvic compression belt.

17. The method according to claim 14 wherein said belt body comprises an attachment surface that spans an entire length of the belt body.

18. The method according to claim 14, wherein said first tightening member is constructed and arranged to continuously engage said belt body along its length.

* * * * *